(12) United States Patent
Denzinger et al.

(10) Patent No.: US 12,354,269 B2
(45) Date of Patent: Jul. 8, 2025

(54) COMPUTER-IMPLEMENTED METHOD FOR EVALUATING A THREE-DIMENSIONAL ANGIOGRAPHY DATASET, EVALUATION SYSTEM, COMPUTER PROGRAM AND ELECTRONICALLY READABLE STORAGE MEDIUM

(71) Applicant: Siemens Healthineers AG, Forchheim (DE)

(72) Inventors: Felix Denzinger, Nuremberg (DE); Michael Wels, Bamberg (DE); Michael Suehling, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 463 days.

(21) Appl. No.: 17/948,452

(22) Filed: Sep. 20, 2022

(65) Prior Publication Data

US 2023/0086196 A1 Mar. 23, 2023

(30) Foreign Application Priority Data

Sep. 22, 2021 (EP) ..................... 21198163

(51) Int. Cl.
*G06K 9/00* (2022.01)
*G06T 7/00* (2017.01)
(Continued)

(52) U.S. Cl.
CPC .......... *G06T 7/0014* (2013.01); *G06V 10/764* (2022.01); *G16H 50/20* (2018.01);
(Continued)

(58) Field of Classification Search
CPC .............. G06T 7/0014; G06T 2200/04; G06T 2207/10081; G06T 2207/30101;
(Continued)

(56) References Cited

U.S. PATENT DOCUMENTS

2021/0166389 A1   6/2021   Denzinger et al.

FOREIGN PATENT DOCUMENTS

CA          2694166 A1 *   2/2008   ............. A61B 6/032
CA          3136976 A1 *  10/2020   ........... A61B 3/0025
(Continued)

OTHER PUBLICATIONS

Hanna R. et al.: "A Hybrid Method for Automatic Anatomical Variant Detection and Segmentation", FIMH 2011: Functional Imaging and Mod-eling of the Heart, pp. 333-340.
(Continued)

*Primary Examiner* — Xin Jia
(74) *Attorney, Agent, or Firm* — Harness, Dickey & Pierce, P.L.C.

(57) ABSTRACT

A computer-implemented method for evaluating a three-dimensional angiography dataset of a blood vessel tree of a patient, comprises determining a variant information describing a belonging to at least one anatomical variant class of a plurality of anatomical variant classes relating to anatomical variants of the blood vessel tree based on a
(Continued)

comparison of angiography information of the angiography dataset to reference information describing at least one of the anatomical variant classes.

20 Claims, 3 Drawing Sheets

(51) Int. Cl.
*G06V 10/764* (2022.01)
*G16H 50/20* (2018.01)
*G16H 50/30* (2018.01)

(52) U.S. Cl.
CPC ......... *G16H 50/30* (2018.01); *G06T 2200/04* (2013.01); *G06T 2207/10081* (2013.01); *G06T 2207/30101* (2013.01); *G06T 2207/30172* (2013.01); *G06V 2201/03* (2022.01)

(58) Field of Classification Search
CPC . G06T 2207/30172; G06T 2207/30048; G06T 2207/30104; G06T 2207/20081; G06T 2207/20084; G06V 10/764; G06V 2201/03; G16H 50/20; G16H 50/30; G06F 18/24317; G06F 18/2433; G06F 18/285
See application file for complete search history.

(56) References Cited

FOREIGN PATENT DOCUMENTS

| CN | 106097298 A | * | 11/2016 | ........... G06T 7/0012 |
|---|---|---|---|---|
| CN | 110264427 A | * | 9/2019 | |
| EP | 3828817 A1 | | 6/2021 | |

OTHER PUBLICATIONS

Fischer, P. et al.: "Deep Learning Based Automated Coronary Labeling For Structured Reporting of Coronary CT Angiography in Accordance With SCCT Guidelines" Journal of Cardiovascular Computed Tomography 14.3 (2020): S21-S22.

Zheng Yefeng: "Robust and Accurate Coronary Artery Centerline Extraction in CTA by Combining Model-Driven and Data-Driven Approaches" Advances in Communication Networking : 20TH Eunice/IFIP EG 6.2, 6.6 International Workshop, Rennes, France, Sep. 1-5, 2014, Revised Selected Papers; [Lecture Notes in Computer Science, ISSN 1611-3349], Springer Verlag, DE, pp. 74-81, XP047042220; 2013.

Lugauer, Felix et al. "Precise Lumen Segmentation in Coronary Computed Tomography Angiography", 2014, Springer, pp. 137-147.

* cited by examiner

COMPUTER-IMPLEMENTED METHOD FOR EVALUATING A THREE-DIMENSIONAL ANGIOGRAPHY DATASET, EVALUATION SYSTEM, COMPUTER PROGRAM AND ELECTRONICALLY READABLE STORAGE MEDIUM

CROSS-REFERENCE TO RELATED APPLICATION(S)

The present application claims priority under 35 U.S.C. § 119 to European Patent Application No. 21198163.4, filed Sep. 22, 2021, the entire contents of which are incorporated herein by reference.

FIELD

One or more example embodiments of the present invention concerns a computer-implemented method for evaluating a three-dimensional angiography dataset, in particular computed tomography angiography dataset, of a blood vessel tree of a patient, in particular the coronary artery tree. One or more example embodiments of the present invention further concerns an evaluation system, a computer program, and an electronically readable storage medium.

BACKGROUND

Medical imaging is an often-used tool for many medical tasks, in particular diagnosis and/or treatment planning and monitoring. In particular, angiography describes techniques, in particular using a contrast agent, to acquire angiography datasets of blood vessels of a patient, in particular at least one blood vessel tree. Two main fields of application regarding angiography comprise coronary angiography and cerebral angiography, for example in the case of strokes.

Regarding coronary angiography, coronary heart disease is one of the major causes of death worldwide. It is associated with atherosclerotic plaques that narrow the blood vessels. These plaques may, for example, arise due to inflammation or disturbances in the blood flow. Recent research shows promising results for the identification of culprit lesions, which may require invasive procedures and/or drug treatment, using the non-invasive diagnostic process of coronary tomography angiography (CCTA). In particular, deep learning approaches have been proposed to evaluate coronary computed tomography angiography datasets using respective evaluation algorithms to, for example, detect lesions in the heart or the coronary artery tree. It has even been proposed to simulate the hemodynamics based on angiography datasets of the heart area, for example to measure hemodynamic parameters like the fractional flow reserve (FFR).

Generally, the physiological task of the coronary arteries is to perfuse the heart muscle, in particular the myocardium. The coronary artery tree comprises three main coronary branches, namely the right coronary artery (RCA), the left anterior descending (LAD), and the ramus circumflexus or circumflex branch of the left coronary artery (LCX), which enclose the whole heart. Labelling schemes for segments in the coronary tree have been proposed by multiple societies and organizations.

Although a definition of a normal anatomy for the main branches exists, several non-pathological normal variants of this anatomy can be present in a patient. Such anatomical variants include different branches being different main contributors for the perfusion of certain heart regions, the presence of an extra branch between the LAD and the LCX, a Uformed loop at the beginning of the RCA (so-called shepherd's crook), a high take-off of a coronary ostium and an acute take-off of the LCX. Comparable anatomical variants also exist in blood vessel trees of the brain.

Information regarding the presence of such normal, that is non-pathological, anatomical variants may be expedient regarding several diagnostic and/or planning tasks. Even though these normal anatomical variants are non-pathological, they may be relevant for patient risk stratification and management decisions. In addition, they can complicate minimally invasive interventions. Hence, they should be included in reports. In another aspect, since anatomical variants may alter the course of the blood flow, they may influence the outcome of evaluation algorithms, in particular regarding deep learning-based approaches and/or hemodynamic FFR calculations.

Today, the presence anatomical variant is qualitatively assessed by a human reader of the anatomy dataset. Regarding single organs, for example the heart, approaches on automatical detection of anatomical variants have recently become known. For example, in an article by R. Hannah et al., "A Hybrid Method for Automatic Anatomical Variant Detection and Segmentation", FIMH 2011: Functional Imaging and Modeling of the Heart, pages 333-340, to cope with topological organ variability, it is proposed to create a set of organ model variants and selecting the most appropriate model variant for the patient at hand.

SUMMARY

One or more example embodiments of the present invention provide a robust approach for automatically assessing the presence of anatomical variants in a blood vessel tree.

Advantages are provided by a computer implemented method, an evaluation system, a computer program and an electronically readable storage medium according to the independent claims. Advantageous embodiments are described in the dependent claims.

According to one or more example embodiments, a computer-implemented method for evaluating a three-dimensional angiography dataset of a blood vessel tree of a patient, includes determining a variant information describing a belonging to at least one anatomical variant class of a plurality of anatomical variant classes relating to anatomical variants of the blood vessel tree based on a comparison of angiography information of the angiography dataset to reference information describing at least one of the anatomical variant classes.

According to one or more example embodiments, the method further includes performing a comparison indicating a presence of anatomical variants; and performing at least one further comparison if anatomical variants are detected in the comparison, the determining determines the belonging to the at least one anatomical variant class relating to anatomical variants as the variant information, wherein if no anatomical variants are detected in the comparison, the determining determines the belonging to the at least one anatomical variant class relating to no anatomical variants as the variant information.

According to one or more example embodiments, the method further includes determining at least one structural information of the blood vessel tree by at least one structural evaluation algorithm as the angiography information.

According to one or more example embodiments, the method further includes determining centerlines for at least a part of blood vessels of the blood vessel tree as structural information to form a centerline tree; providing at least one rule set for at least one of the anatomical variant classes as reference information, each rule set comprising at least one condition for at least one feature of the centerline tree, wherein the comparison includes, applying the conditions of at least one of the at least one rule set, and determining the belonging to the at least one anatomical variant class to be associated with a rule set when all conditions of the rule set associated with the anatomical variant class are fulfilled by the centerline tree.

According to one or more example embodiments, at least one condition evaluates anatomy information describing at least one additional anatomical feature, which is not part of the blood vessel tree, and the anatomy information is derived from at least one of the angiography dataset or an additional image data set registered with the angiography dataset.

According to one or more example embodiments, the method further includes providing at least one anatomical atlas dataset relating to at least one anatomical variant class as reference information; and comparing the anatomical atlas dataset to at least one of the at least one angiography dataset or a comparison dataset derived therefrom as angiography information.

According to one or more example embodiments, the providing provides a no variant anatomical atlas dataset relating to no anatomical variants, the no variant anatomical atlas dataset is derived statistically from multiple base datasets of patients showing no anatomical variants.

According to one or more example embodiments, the method further includes performing a comparison indicating a presence of anatomical variants and if no anatomical variants are detected in the performed comparison, a belonging to an anatomical variant class relating to no anatomical variants is determined as the variant information, and if anatomical variants are detected in the performed comparison, the determining determines the belonging to at least one other anatomical variant class by at least one further comparison with the no variant anatomical atlas dataset restricted to a subarea of the blood vessel tree, wherein the subarea is associated with at least one anatomical variant class, to determine if the angiography dataset belongs to the associated anatomical variant class.

According to one or more example embodiments, the method further includes at least one of calculating at least one similarity metric correlation metric and used in the comparison indicating a presence of anatomical variants or deriving a lumen of blood vessels of the blood vessel from the angiography dataset used as the comparison dataset.

According to one or more example embodiments, the method further includes using the variant information for at least one of automatic report generation or to determine an applicability of a downstream evaluation algorithm.

According to one or more example embodiments, the method further includes using at least one anatomical variant class relating to an image feature in the angiography dataset caused by an imaging artifact.

According to one or more example embodiments, at least one anatomical variant class relates to at least one of at least one dominance variant, at least one region supply variant, at least one additional or less blood vessel variant, at least one course variant, or at least one ostium anomaly variant.

According to one or more example embodiments, an evaluation system for evaluating a three-dimensional angiography dataset of a blood vessel tree of a patient, includes a first interface configured to receive the angiography dataset; a determination unit configured to determine a variant information describing a belonging to at least one anatomical variant class of a plurality of anatomical variant classes relating to anatomical variants of the blood vessel tree based on a comparison of angiography information of the angiography dataset to reference information describing at least one of the anatomical variant classes; and a second interface configured to provide the variant information.

According to one or more example embodiments, a non-transitory electronically readable storage medium has a computer program that, when executed by a computing device of an evaluation system, causes the evaluation system to perform a method according to one or more example embodiments.

BRIEF DESCRIPTION OF THE DRAWINGS

Objects and features of one or more example embodiments of the present invention will become apparent from the following detailed description considered in conjunction with the accompanying drawings. The drawings, however, are only principle sketches designed solely for the purpose of illustration and do not limit the present invention. The drawings show.

DETAILED DESCRIPTION

Figure 1:
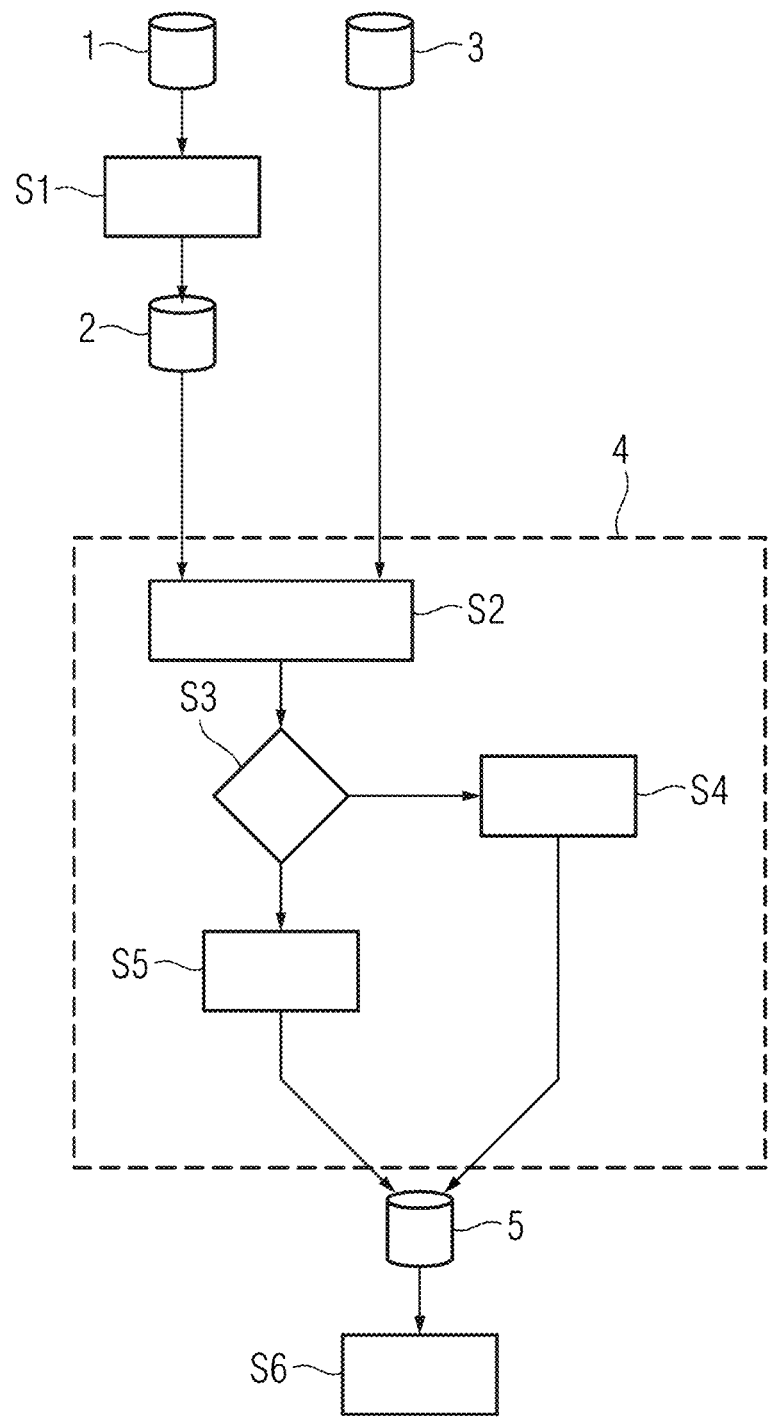
FIG. 1 a flow chart of a method according to one or more example embodiments of the present invention, FIG. 2 a schematical drawing illustrating a first anatomical variant according to one or more example embodiments of the present invention, FIG. 3 a schematical drawing illustrating a second anatomical variant according to one or more example embodiments of the present invention, FIG. 4 a schematical drawing illustrating a third anatomical variant according to one or more example embodiments of the present invention, FIG. 5 a schematical drawing illustrating a fourth anatomical variant according to one or more example embodiments of the present invention, and FIG. 6 the functional structure of an evaluation system according to according to one ore more example embodiments of the present invention.

In a method as initially described, a variant information describing the belonging to at least one anatomical variant class of a plurality of anatomical variant classes relating to anatomical variants of the blood vessel tree is determined based on a comparison of angiography information of the angiography dataset to reference information describing at least one of the anatomical variant classes.

One or more example embodiments of the present invention determines the presence of variants based on a comparison to reference information, wherein, in preferred embodiments, the comparison is based on structural features of the blood vessel tree. That is, the structure of the blood vessel tree may be analysed in a first, preparatory step. In particular, at least one structural information of the blood vessel tree may be determined by at least one structural evaluation algorithm as the angiography information. This angiography information is then compared to reference information, which also comprises or refers to such structural features. Hence, in one or more example embodiments of the present invention, it is preferably the structure, in particular concrete structural features like centerlines and/or the lumen of the blood vessels, which have been identified as carrying all relevant information needed to determine the presence of anatomical variants, as will be shown in detail below.

In this manner, the presence of anatomical variants can be determined in a fully automated fashion and allowing an easy and robust implementation. The detection and labelling of anatomical variants, in addition to pathology and patient-specific anatomy, introduces a new general semantic concept, which may, for example, be exploited in computer-aided detection (CADe). Medical staff, in particular a physician treating the patient, is provided with additional, clinically relevant information which can be taken into account in diagnosis and/or, in particular, treatment planning, for example regarding minimally invasive interventions.

The general approach of the current invention is applicable to any blood vessel tree and any imaging modality, however, a preferred field of application are computed tomography angiography results regarding the coronary artery tree or blood vessel trees in the brain.

In a generally applicable, advantageous embodiment of the current invention, in a first step, a comparison indicating the general presence of anatomical variants is performed, wherein, if no anatomical variants are detected in the comparison, a belonging to an anatomical variant class relating to no anatomical variants is determined as the variant information, and else, in a second step, the belonging to at least one other anatomical variant class is determined by at least one further comparison. That is, a normal anatomy can be defined, for example, by choosing, for each possible sort of anatomical variant, the option having the highest prevalence among patients. Such normal anatomies have already been defined in the art and may form a basis for a first comparison. If this first comparison indicates that no deviations pointing to the presence of anatomical variants differing from this normal anatomy are present, this result may already be used to determine the variant information, such that no further comparisons are required. Hence, in many cases, computational effort and time can be saved. In embodiments, further comparisons may be specifically conducted regarding single anatomical variant classes or groups of anatomical variant classes, wherein, of course, comparison information of the first comparison in the first step may be evaluated to select for which anatomical variant classes further comparisons are performed. Of course, further hierarchically structured comparisons in multiple second steps are also possible, for example performing one comparison for a group of anatomical variant classes, wherein comparisons for members of the group are only performed if the group comparison returned the presence of at least one anatomical variant of the group.

In the following, two concrete, advantageous embodiments of the inventive idea are explained in detail, which may also be used cumulatively, that is, different of the two concrete approaches may be used for different classes of anatomical variants and/or different comparison hierarchy levels and/or both concrete approaches may be applied for at least one anatomical variant class, for example to allow a plausibility check and/or further improved robustness.

In a first approach, which is especially advantageously applicable to evaluations of the coronary artery tree, for example, coronary computed tomography angiography datasets (CTTA datasets), centerlines for at least a part of the blood vessels of the blood vessel tree are determined as structural information to form a centerline tree, wherein as reference information at least one rule set for at least one of the anatomical variant classes is provided, each rule set comprising at least one condition for at least one feature of the centerline tree, wherein, in the comparison, the conditions of at least one of the at least one rule set are applied and belonging to an anatomical variant class associated with a rule set is determined when all conditions of the rule set associated with the anatomical variant class are fulfilled by the centerline tree.

In the course of one or more example embodiments of the present invention, it was understood that, regarding blood vessel trees, in particular the coronary artery tree, centerlines, while being a simple and easy to handle geometrical construct, contain all information relevant for typical normal classes of anatomical variants. In additions, for the centerlines of a centerline tree, conditions may be formulated which, when they are all fulfilled, indicate presence of a certain anatomical variant. In preferred embodiment, also additional anatomical features derivable from the anatomy dataset can be taken into account in rule sets, that is, in preferred embodiments, at least one condition evaluates anatomy information describing at least one additional anatomical feature, which is not part of the blood vessel tree, wherein the anatomy information is derived from the angiography dataset and/or an additional image dataset registered with the angiography dataset. For example, if it is to be determined which blood vessel mainly supplies a predefined region, the region may be segmented and distance of centerlines to the regions may be compared, concluding that the vessel whose centerline is closest to the region is the vessel mainly supplying the region. In other examples, relative positions to more than additional anatomical feature may be evaluated.

In general examples, at least one condition may compare at least one angle at a bifurcation (or multifurcation) to a threshold angle and/or at least one curvature in at least one vessel segment to a threshold curvature and/or at least one number of multifurcations in at least one vessel segment with a reference number and/or distances between centerline tree features and/or at least one additional anatomy feature described by anatomy information derived from the angiography dataset and/or the additional image dataset and/or may check the presence of at least one type of multifurcation, in particular trifurcation.

It should be noted at this point that, generally, a segment labelling algorithm may be applied to the centerline tree. Such segment labelling algorithms are known from the state of the art and may be applied to locate segments requested by conditions for a comparison. As an example, it is referred to the Article by A. Fischer et al., "Deep Learning Based Automated Coronary Labeling For Structured Reporting Of Coronary CT Angiography In Accordance With SCCT Guidelines", Journal of Cardiovascular Computed Tomography 14.3 (2020), pages 21-22. Regarding centerline extraction algorithms, it is exemplarily referred to Y. Zheng et al. "Robust and Accurate Coronary Artery Centerline Extraction in CTA by Combining Model-Driven and Data-Driven Approaches", International Conference on Medical Image Computing and Computer-Assisted Intervention, pages 74-81, Nagoya.

In a second concrete approach, which can be especially advantageously applied to blood vessel trees in the brain, at least one anatomical atlas dataset relating to at least one anatomical variant class may be provided as reference information, wherein the anatomical atlas dataset is compared to the at least one angiography dataset or a comparison dataset derived therefrom as angiography information. In other words, an atlas of possible anatomical variants of the blood vessel tree can be registered to the angiography information. In an embodiment, the atlas version associated with at least one anatomical variant class having the least distance to the actual anatomy information should represent the anatomical variants at hand. For example, anatomical atlas datasets may be derived statistically from multiple base datasets of other patients showing the respective anatomical variants/anatomical variant configurations.

In particular, a no variant anatomical atlas dataset relating to no anatomical variants (that is, no (relevant) deviations from a predefined normal anatomy), may be used, which may be derived statistically from multiple base datasets of patients showing no anatomical variants. Such an anatomical atlas dataset relating to the normal anatomy is particularly advantageous with respect to the above-discussed two-step comparison configuration, that is, in an advantageous embodiment,
if, in a first step, a comparison indicating the general presence of anatomical variants is performed, wherein, if no anatomical variants are detected in the comparison, a belonging to an anatomical variant class relating to no anatomical variants is determined as the variant information, and else, in a second step, the belonging to at least one other anatomical variant class is determined by at least one further comparison,
in the second step, at least one comparison with the no variant anatomical atlas dataset restricted to a subarea of the blood vessel tree, wherein the subarea is associated with at least one anatomical variant class, is performed to determine if the angiography dataset belongs to the associated anatomical variant class.

Hence, the no variant anatomical atlas dataset may be used in the first step to generally check whether deviations from the predefined normal anatomy are present. If it is found that no (relevant) deviations are present, that is, the patient has normal anatomy, no further comparison in a second step is necessary. If, however, deviations are found, further comparisons ensue in the second step. Here, the fact that the anatomical variants of the respective anatomical variant classes are localized can be exploited in that comparisons for subareas in the blood vessel tree can be performed. If, for example, an anatomical variant class relating to a specific course of a vessel is found in a certain segment, the comparison regarding this anatomical variant class may be restricted to the subarea in which the segment is found. If no other anatomical variant classes are localized to this subarea, a deviation would indicate that the course of the segment does actually differ from the norm.

It is noted that, in such an embodiment, but also generally, at least one similarity metric and/or correlation metric may be calculated and used in the comparison. For example, when comparing to the no variant anatomical atlas dataset, a threshold for the similarity measure may be defined which, when it is exceeded, indicates that a normal anatomy can be assumed. Of course, in embodiments, multiple similarity and/or correlation metrics may be used which, if deviation from the predefined normal anatomy is determined in the first step, may already allow to predict which anatomical variants may be present, such that, for example, the associated anatomical variant classes may be selected for further comparisons and others may be excluded. Furthermore, anatomical variant classes to be checked in the second step may be prioritized depending on the actual value of the at least one similarity and/or correlation matric.

In especially preferred embodiments of the second approach, also, structural information is used as the basis of comparison. Preferably, the lumen of the blood vessels of the blood vessel tree are derived from the angiography dataset as a structural information and used as comparison dataset. That is, the lumen of the vasculature is extracted using lumen extraction algorithms known in the art. For example, since a contrast agent has been used, the lumen may be determined in a segmentation process. Afterwards, the at least one anatomical atlas dataset may be registered to this segmentation. In this manner, also for the second approach, the data to be compared may be limited to actually relevant information.

Regarding lumen detection algorithms, it is referred to F. Lugauer et al., "Precise lumen segmentation in coronary computed tomography angiography", International MICCAI Workshop on Medical Computer Vision, pages 137-147, Springer (2014).

In preferred embodiments, the variant information may be used for automatic report generation and/or to determine the applicability of a downstream evaluation algorithm, in particular a deep learning-based artificial intelligence evaluation algorithm. The method described here thus allows for automated report generation which, for example, allows to inform medical staff that a certain anatomical variant might complicate a planned medical procedure. Furthermore and especially preferred, the variant information can work as a "gatekeeper" for other evaluation algorithms, especially deep learning-based approaches which may have problems if input data is not represented well in the training data. If, for example, an evaluation algorithm has only been trained regarding specific anatomical variant configurations, problems may arise if a new anatomical variant configuration is used as input data. In this case, user information may be output regarding the evaluation algorithm, for example pointing to a lower reliability of results and/or prompting manual evaluation, in particular by reading, instead. Such a "gatekeeper" functionality increases the confidence of clinicians towards the use of related deep learning-based approaches. Examples for such evaluation algorithms comprise deep learning-based FFR calculation and lesion detection algorithms.

In a further preferred embodiment of the present invention, at least one anatomical variant class relating to an image feature in the angiography dataset caused by an imaging artifact, in particular a stack artifact, is used. Some image artifacts, in particular the so-called stack artifacts, take the appearance of anatomical variants in the angiography dataset. Hence, the strategy according to one or more example embodiments of the present invention can also be applied to artifact detection in angiography datasets, as imaging artifacts may share similar morphological manifestations in the angiography data as anatomical variants, for example gaps and/or offsets in the depicted blood vessels. If, for example the angiography dataset is compiled from at least two image stacks, due to various causes in the imaging procedure, a gap or offset may occur, leading, for example, to a separation of two parts of a blood vessel. This is called a stacking artifact and may also be detected using the current invention. Other examples for imaging artifacts may be localized blurring artifacts, if, for example, a blurred streak in the image causes the vessel wall to be less sharp, as if contrast agent has penetrated. Such artifacts may also be assigned an anatomical variant class and may be detected using the current invention. The detection of such an imaging artifact may lead to a corresponding user information, such that a user can distinguish between real anatomical variants and anatomical abnormalities caused by imaging artifacts.

As already explained, at least one anatomical variant class may relate to normal anatomical variants, that is, anatomical variants which are not pathological. As concrete examples for anatomical variants in blood vessel trees, at least one anatomical variant class may relate to at least one dominance variant and/or at least one region supply variant and/or at least one additional and/or less blood vessel variant and/or at least one course variant and/or at least one ostium anomaly variant. For example, in the case of the coronary artery tree, different vessels may dominate the perfusion, wherein by definition, dominance is determined by the vasculature side which supplies the back side of the heart. While, in most of the cases, having a prevalence of 70% and thus being the normal case, there is right dominance, with a prevalence of 10%, left dominance is observed, and with a prevalence of 20%, even codominance may occur. Codominance means that the posterior descending artery (PDA) and posterolateral branches arise from both right and left vasculature. Which dominance is present in a patient may, for example, be detected by extracting the centerlines and perform rule-based analysis of the centerline courses. The dominance side should have a posterior descending artery (PDA) segment and, in the codominant case, both PDA should exist.

Further anatomical variants concern the supply of different regions. For example, the inferior wall supply may be analyzed. If, for example, the PDA has a premature take-off and then courses towards the cardiac apex along the diaphragmatic surface of the right ventriculum (RV), the anatomical variant may be called "early takeoff of the PDA". In another variant, the LAD may wrap around the cardiac apex and supply a part of the apical inferior wall, known as "wraparound LAD". Finally, there can be multiple branches, in which the case the PDA is very small and multiple branches from the distal RCA, LCX (left circumflex artery) and obtuse marginal branches may supply the inferior wall. In another example, the atrioventricular nodal supply can be analysed. The blood supply to the atrioventricular node is with a prevalence of 90% from the atrioventricular nodal branch of the RCA or, with the prevalence of 10%, the LCX. As a final example, the sinoaterial nodal supply may be analysed, that is, which main coronary artery supplies the sinoaterial node. With a prevalence of 60%, this will be the RCA, while in some cases, it may also be the distal RCA or LCX. Regarding such region supply variants, in the first approach, detection may be based on segmenting the supply region of interest as additional anatomical feature, wherein the closest centerline of the extracted centerlines of the centerline tree can be identified, since the condition for having a certain blood vessel mainly supplying the supply region of interest may be that its centerline is the closest to the supply region of interest.

In another general group of anatomical variants, there may be additional, that is excess blood vessels, or less blood vessels, that is, a blood vessel may be missing. A prominent example in the coronary case is the so-called Ramus Intermedius, wherein the left main coronary artery (LMCA) does not bifurcate into LCX and LAD, but trifurcates into LCX, LAD and additionally the Ramus Intermedius. This can be detected by analysis of the centerline tree structure, namely if a trifurcation after the LMCA is present.

An example for a missing blood vessel (segment) is the so-called LMCA (left main coronary artery) atresia, in which the LMCA is absent and LAD and LCX arise from separate, but adjacent ostia in the left sinus of valsalva (LSV). This may be detected if multiple ostia for the left side arteries are found, for example, in the centerline tree or the lumen comparison dataset.

Regarding course variants, examples include myocardiac bridging. Such an anatomical variant can be found with a prevalence of up to 25%. In myocardiac bridging, an atypical course of a coronary artery is found, in which it dips intramyocardially with resulting compression of the vessel during systole. In the first approach using the centerline tree, this can be detected by also segmenting the myocard as additional anatomical feature and providing respective anatomy information, wherein the condition checks whether the centerline of the blood vessel runs through the segmented myocard mask.

In another example of a course variant, the LCX may show an acute take-off. This anatomical variant features an angle of less than 45° between LMCA and LCX. This can also be detected in a simple manner from the centerline tree, as a condition may simply evaluate the angle at the bifurcation and check whether it is below or equal to the threshold of 45°.

A well-known further course variant is the shepherd's crook in the RCA, which has a prevalence of about 5%. In this anatomical variant, the RCA has a normal origin, but takes a tortuous and high course, usually immediately after it originates from the aorta. While this can be determined from a centerline tree (in particular after applying a segment labelling algorithm) by analysing the curvature, additionally or alternatively, also the centerline course may be analysed with respect to the aorta as further anatomical feature. For example, the RCA may stay close to the aorta for couple of millimeters, while the distance to the heart (which may also be segmented) increases in the beginning of the RCA.

Finally, ostia anomalies can be detected as anatomical variants. For example, in an anatomical variant known as "high take-off", the position of an ostium may be 5 mm or more above the aortic sinotubular junction. This may also be detected by centerline course analysis, for example when it is detected that the RCA is adjacent to the aorta for the first few millimeters, closing in on the heart.

As a final example, duplication of a blood vessel should be mentioned, for example a slit RCA. Such an anatomical variant may be defined as an RCA that features a split PDA with the interior subdivision of the RCA leading to the distal portion of the PDA leading to the interior free wall of the right ventriculum. The other (posterior) bifurcation of the RCA maintains a course in the atrioventricular groove and forms the uppermost portion of the posterior descending branch. This is also known as "double RCA". It may be detected by centerline course analysis.

Regarding the second approach, in an embodiment where subareas are compared in a second comparison step, the example discussed here can be localized in the sense that a deviation in an associated subarea is typical for the presence of the respective anatomical variant. Regarding blood vessel trees in the brain, like anatomical variants are known.

One or more example embodiments of the present invention further concerns an evaluation system for evaluating a three-dimensional angiography dataset, in particular computer tomography angiography dataset, of a blood vessel tree of a patient, in particular the coronary artery tree, comprising:

a first interface for receiving the angiography dataset,
a determination unit for determining a variant information describing the belonging to at least one anatomical variant class of a plurality of anatomical variant classes relating to anatomical variants of the blood vessel tree based on a comparison of angiography information of the angiography dataset to reference information describing at least one of the anatomical variant classes, and
a second interface for providing the variant information.

The determination unit can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the present invention.

The term "unit" may be replaced with the term "circuit" or "module". The term "unit" may refer to, be part of, or include processor hardware (shared, dedicated, or group) that executes code and memory hardware (shared, dedicated, or group) that stores code executed by the processor hardware.

The unit may be implemented in one control unit and may include one or more interface circuits. Different components of the system may be implemented in a delocalized system, e.g. in a network. In some examples, the interface circuits may include wired or wireless interfaces that are connected to a local area network (LAN), the Internet, a wide area network (WAN), or combinations thereof. The functionality of any given unit of the present disclosure may be distributed among multiple modules that are connected via interface circuits. For example, multiple modules may allow load balancing. In a further example, a server (also known as remote, or cloud) module may accomplish some functionality on behalf of a client module.

In other words, the evaluation system may comprise a computing device configured to perform a method according to one or more example embodiments of the present invention. All features and remarks relating to the method according to one or more example embodiments of the present invention correspondingly apply to the evaluation system according to one or more example embodiments of the present invention.

The evaluation system may, as a computing device, comprise at least one processor and at least one storage means, wherein, for example, the reference information may be stored in the storage means. The functional units may be realized as hardware and/or software. Furthermore, other functional units and/or subunits may be added for implementing steps of preferred embodiments of the method according to the present invention.

The evaluation system may, for example, be integrated in an imaging system, for example a computer tomography device. However, in preferred embodiments, the evaluation system may be included into a reading workstation such that variant information may be provided to a person reading angiography datasets, for example a radiologist. In embodiments, the evaluation system may, of course, also provide further evaluation information by employing corresponding evaluation algorithms.

A computer program according to one or more example embodiments of the present invention can be directly loaded into the computing device of an evaluation system and comprises program means such that the computing device performs the steps of a method according to one or more example embodiments of the present invention when the computer program is executed on the computing device of the evaluation system. The computer program may be stored on an electronically readable storage medium according to one or more example embodiments of the present invention, which thus comprises control information such that, when the electronically readable storage medium is used in a computing device of an evaluation system, the steps of a method according to one or more example embodiments of the present invention are performed. The electronically readable storage medium according to one or more example embodiments of the present invention may be a non-transitory medium, for example a CD-ROM.

In the following the solution according to one or more example embodiments of the present invention is described and claimed with respect to systems as well as with respect to methods. Elements, characteristics, advantages or alternative embodiments herein can be assigned to the other claimed objects and vice versa. In other words, claims for the evaluation system can be improved with features described or claimed in the context of the methods and vice versa. The functional features of the method are embodied by objective units of the providing system. Furthermore, elements, characteristics, advantages or alternative embodiments described in connection with particular exemplary embodiments can be assigned to the invention in its most general terms.

FIG. 1 is a general flow chart of preferred embodiments of a method according to one or more example embodiments of the present invention. In the method, an angiography dataset 1, in this case a computer tomography angiography dataset, is evaluated regarding the presence of anatomical variants with respect to a predefined normal anatomy. The angiography dataset 1 shows a blood vessel tree in an imaging region of a patient. In the following, exemplarily, it is referred to the coronary artery tree as blood vessel tree, however, in other embodiments, the blood vessel tree can also comprise blood vessels in the brain of the patient.

In a preparatory step S1, structural information is determined from the angiography dataset 1, which will, in the following, be used as angiography information 2 to be compared with reference information 3 regarding to at least one anatomical variant class. In preferred embodiments, centerlines can be extracted in step S1 using a centerline extraction algorithm, such that a centerline tree results, and/or a lumen extraction algorithm can be employed to segment the lumen of the blood vessels of the blood vessel tree. Additionally, preferably, a segment labelling algorithm may be applied to assign centerlines and/or lumens to segments, in particular according to a labelling scheme. This is useful if, in the comparison 4, in particular in conditions of a rule set, centerlines of defined segments are to be analysed.

In FIG. 1, a two-step comparison 4 is exemplarily shown. In a first comparison step S2, a comparison indicating the general presence of anatomical variants is performed. This can, for example, be done by comparing a lumen dataset as angiography information 2 with a no variant anatomical atlas dataset (showing the predefined normal anatomy) of the reference information 3. Additionally or alternatively, a rule set of the reference information 3 using conditions indicating the presence of no variants if fulfilled may be applied. In any case, if it is determined as a result of step S2 that no variants are present in a step S3, a variant information 5 is determined in step S4 such that it indicates this presence of no anatomical variants regarding the predefined normal anatomy.

If, however, the first comparison in step S2 has indicated that anatomical variants are present, in a second comparison step S5, at least one other anatomical variant class is determined into which the anatomical variants fall. In any case, the variant information 5 indicates the presence of anatomical variants of at least one anatomical variant class or the presence of no anatomical variants with respect to the normal anatomy, that is, no relevant deviations from the normal anatomy, which forms another anatomical variants class indicating no relevant deviations from the predefined normal anatomy.

In an optional step S6, the variant information may be used for further automatical decisions and/or processes. Preferably, the variant information 5 may be used to automatically generate a report also comprising information on anatomical variants, which may be used, for example, regarding the further treatment of the patient, in particular if a minimally invasive intervention is planned. Further preferably, the variant information 5 may be used to determine the applicability of a downstream evaluation algorithm in a "gatekeeper" functionality. For example, if the evaluation function is a deep learning-based artificial intelligence evaluation function, which has been trained using training data not comprising a certain anatomical variant which has now been found, a warning may be output and/or manual reading may be prompted.

It is noted that some anatomical variant classes may also relate to imaging artifacts, which appear like anatomical variants but are caused in the imaging process. An example are stacking artifacts. If such an imaging artifact has been detected, in a step S6, a corresponding user information is output and/or a correction measures may be triggered.

Regarding the comparison in step S4, two advantageous approaches are conceivable, which may also be used in a combination, for example by using an anatomical atlas dataset relating to no anatomical variants for the first comparison in step S2 to angiography information 2 comprising the segmented lumens, while, in the second comparison step S5, the centerline tree is evaluated using conditions of rule sets.

In particular regarding the coronary artery tree, the use of rule sets comprising conditions indicating the presence of an anatomical variant of at least one anatomical variant class if fulfilled has proven particularly advantageous at least in the second step S5, since all relevant information regarding usual anatomical variants is included in the centerline, the connections and their course. Some examples will now be discussed with reference to FIGS. 2 to 5. Generally, types of anatomical variants/anatomical variant classes that may be detected using rule sets, each comprising at least one condition, comprise dominance variants, region supply variants, additional and/or missing blood vessel variants, course variants and ostium anomaly variants.

Figure 2:
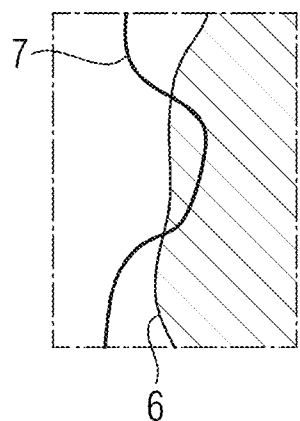
Figure 3:
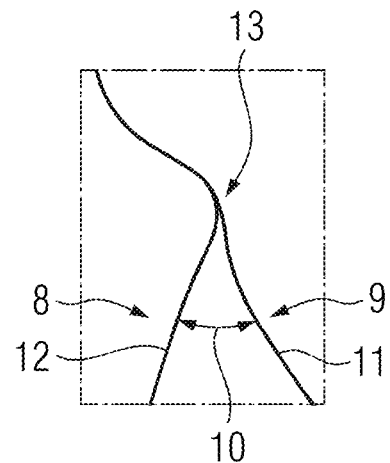
Figure 4:
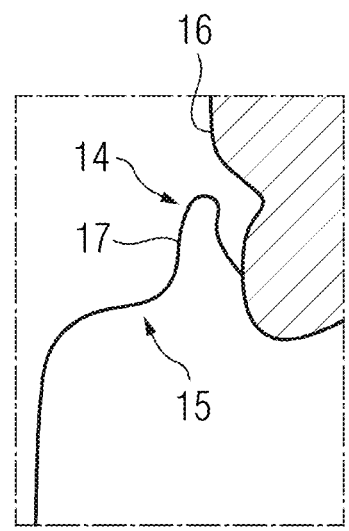

FIGS. 2 to 4 schematically show examples for anatomical variants in the course of a blood vessel, which are chosen to be easily visualizable. FIG. 2 concerns myocardiac bridging. Here, a blood vessel takes it course partly through the myocard, indicated by the segmented region 6. As can be seen, the centerline 7 partly runs through the region 6, clearly indicating the presence of myocardiac bridging.

It is generally noted that, in the step S1 of FIG. 1, anatomy information describing at least one additional anatomical feature, here the myocard, may be determined from the angiography dataset 1 and/or at least one additional image dataset registered to the angiography dataset 1. Of course, anatomy information concerning other anatomical features can also be determined, for example, if it is to be determined which blood vessel supplies a certain supply region of interest, for example the inferior wall, the atrioventricular node and/or the sinoaterial node. In such a case, it can be checked which centerline lies closest to the segmented supply region of interest.

FIG. 3 relates to an acute take-off of the LCX 8 from the LMCA 9. To determine the presence of this anatomical variant, the angle 10 between the respective centerlines 11, 12 at the bifurcation 13 is compared to a threshold angle of 45°. If the angle is smaller or equal 45°, an acute take-off of the LCX is present.

FIG. 4 illustrates a shepherd's crook 14 of the RCA 15 immediately after originating from the aorta 16. Such a shepherd's crook 14 can, for example, be detected by analysing the course, in particular the curvature, of the centerline 17 of the RCA 15 after it originates from the aorta 16.

Figure 5:
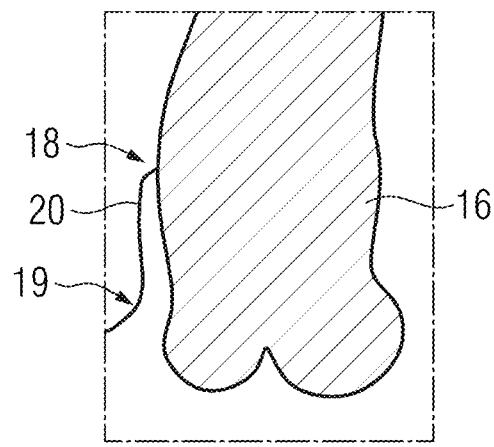

FIG. 5 illustrates so-called high take-off. As can be seen, the ostium 18 of a coronary artery 19 from the aorta 16 is so high such that the coronary artery 19, for example the RCA 15, runs adjacent to the aorta 16 for the first few millimeters, as can be clearly seen from the respective centerline 20.

Regarding the use of anatomical atlas datasets (second approach), it is noted that the comparison can, for example, be executed as a registration of the anatomy information 2, for example the segmented lumens, to the corresponding anatomical atlas dataset of the reference information 3, usually yielding a distance as a similarity and/or correlation metric. For example, multiple different anatomical atlas datasets can be registered to the anatomy information 2 and the at least one anatomical variant class associated with the closest anatomical atlas dataset may be assigned to the angiography dataset 1. However, in a preferred embodiment, in which the different anatomical variants of the anatomical variant classes can be localized differently, comparison with the anatomical atlas dataset relating to no anatomical variants can be repeated for subareas associated with the different anatomical variant classes, so that deviations may be localized and the correspondingly present anatomical variant can be concluded.

Figure 6:
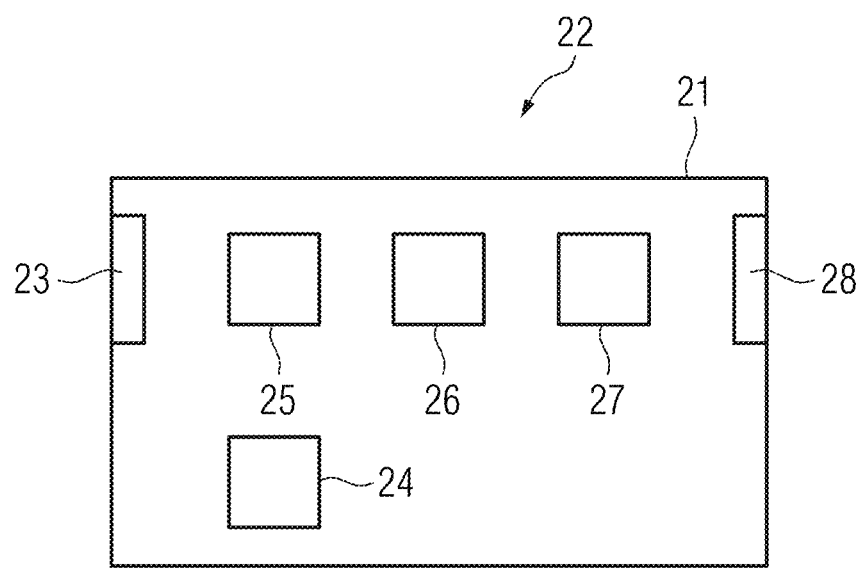

FIG. 6 shows the functional structure of a computing device 21 of an evaluation system 22 according to one or more example embodiments of the present invention. The evaluation system 22 comprises a first interface 23 for receiving angiography datasets 1. Further, in a storage means 24, the reference information 2 can be stored. Received angiography datasets 1 can be processed by a structure extraction unit 25 to determine angiography information 2 in the form of structural information, in particular centerlines and/or lumens, according to step S1.

In a determination unit 26, the variant information 5 is determined by comparison 4, as described above, in particular in steps S2 to S5. In an optional utilization unit 27, the variant information 5 may be further used for automatic report generation, gatekeeper functionality and/or regarding detected imaging artifacts, as described with respect to step S6. A second interface 28 is an output interface, in particular regarding the variant information 5, but also automatically generated report and the like.

The evaluation system 22 may be integrated in an imaging device and/or in a reading workstation. Further, the evaluation system may, of course, offer additional evaluation services, in particular application of evaluation algorithms.

Although some example embodiments of the present invention have been disclosed in the form of preferred embodiments and variations thereon, it will be understood that numerous additional modifications and variations could be made thereto without departing from the scope of example embodiments of the present invention. For the sake of clarity, it is to be understood that the use of "a" or "an" throughout this application does not exclude a plurality, and "comprising" does not exclude other steps or elements. The mention of a "unit", "module" or a "device" does not preclude the use of more than one unit or device.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'unit', interface' or the term 'controller' may be replaced with the term 'circuit.' The term 'module' and may 'unit' refer to, be part of, or include processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been described in detail with reference to example embodiments, the present invention is not limited by the disclosed examples from which the skilled person is able to derive other variations without departing from the scope of the invention.

The invention claimed is:

1. A computer-implemented method for evaluating a three-dimensional angiography dataset of a blood vessel tree of a patient, the method comprising:
   determining a variant information describing a belonging to at least one anatomical variant class of a plurality of anatomical variant classes relating to anatomical variants of the blood vessel tree based on a comparison of angiography information of the angiography dataset to reference information describing at least one of the anatomical variant classes.

2. The computer-implemented method of claim 1, further comprising:
   performing a comparison indicating a presence of anatomical variants; and
   performing at least one further comparison if anatomical variants are detected in the comparison, the determining determines the belonging to the at least one anatomical variant class relating to anatomical variants as the variant information, wherein
   if no anatomical variants are detected in the comparison, the determining determines the belonging to the at least one anatomical variant class relating to no anatomical variants as the variant information.

3. A non-transitory electronically readable storage medium having a computer program that, when executed by a computing device of an evaluation system, causes the evaluation system to perform the method of claim 2.

4. The computer-implemented method of claim 2, further comprising:
   determining at least one structural information of the blood vessel tree by at least one structural evaluation algorithm as the angiography information.

5. The computer-implemented method of claim 2, further comprising:
   providing at least one anatomical atlas dataset relating to at least one anatomical variant class as reference information; and
   comparing the anatomical atlas dataset to at least one of the angiography dataset or a comparison dataset derived therefrom as angiography information.

6. The computer-implemented method of claim 5, wherein the providing provides a no variant anatomical atlas dataset relating to no anatomical variants, the no variant anatomical atlas dataset is derived statistically from multiple base datasets of patients showing no anatomical variants.

7. The computer-implemented method of claim 1, further comprising:
   determining at least one structural information of the blood vessel tree by at least one structural evaluation algorithm as the angiography information.

8. The computer-implemented method of claim 7, further comprising:
   determining centerlines for at least a part of blood vessels of the blood vessel tree as structural information to form a centerline tree; and
   providing at least one rule set for at least one of the anatomical variant classes as reference information, each rule set comprising at least one condition for at least one feature of the centerline tree, wherein
   the comparison includes,
      applying the conditions of at least one of the at least one rule set, and
      determining the belonging to the at least one anatomical variant class to be associated with a rule set when all conditions of the rule set associated with the anatomical variant class are fulfilled by the centerline tree.

9. The computer-implemented method of claim 8, wherein
   at least one condition evaluates anatomy information describing at least one additional anatomical feature, which is not part of the blood vessel tree, and
   the anatomy information is derived from at least one of the angiography dataset or an additional image data set registered with the angiography dataset.

10. The computer-implemented method of claim 7, further comprising:
    providing at least one anatomical atlas dataset relating to at least one anatomical variant class as reference information; and
    comparing the anatomical atlas dataset to at least one of the angiography dataset or a comparison dataset derived therefrom as angiography information.

11. The computer-implemented method of claim 10, wherein the providing provides a no variant anatomical atlas dataset relating to no anatomical variants, the no variant anatomical atlas dataset is derived statistically from multiple base datasets of patients showing no anatomical variants.

12. The computer-implemented method of claim 1, further comprising:
    providing at least one anatomical atlas dataset relating to at least one anatomical variant class as reference information; and
    comparing the anatomical atlas dataset to at least one of the angiography dataset or a comparison dataset derived therefrom as angiography information.

13. The computer-implemented method of claim 12, wherein the providing provides a no variant anatomical atlas dataset relating to no anatomical variants, the no variant anatomical atlas dataset is derived statistically from multiple base datasets of patients showing no anatomical variants.

14. The computer-implemented method of claim 13, further comprising:
    performing a comparison indicating a presence of anatomical variants and if no anatomical variants are detected in the performed comparison, a belonging to an anatomical variant class relating to no anatomical variants is determined as the variant information, and
    if anatomical variants are detected in the performed comparison, the determining determines the belonging to at least one other anatomical variant class by at least one further comparison with the no variant anatomical atlas dataset restricted to a subarea of the blood vessel tree, wherein the subarea is associated with at least one anatomical variant class, to determine if the angiography dataset belongs to the associated anatomical variant class.

15. The computer-implemented method of claim 12, further comprising:
at least one of calculating at least one similarity metric correlation metric and used in the comparison indicating a presence of anatomical variants or deriving a lumen of blood vessels of the blood vessel from the angiography dataset used as the comparison dataset.

16. The computer-implemented method of claim 1, further comprising:
using the variant information for at least one of automatic report generation or to determine an applicability of a downstream evaluation algorithm.

17. The computer-implemented method of claim 1, further comprising:
using at least one anatomical variant class relating to an image feature in the angiography dataset caused by an imaging artifact.

18. The computer-implemented method of claim 1, wherein
at least one anatomical variant class relates to at least one of,
at least one dominance variant,
at least one region supply variant,
at least one additional or less blood vessel variant,
at least one course variant, or
at least one ostium anomaly variant.

19. A non-transitory electronically readable storage medium having a computer program that, when executed by a computing device of an evaluation system, causes the evaluation system to perform the method of claim 1.

20. An evaluation system for evaluating a three-dimensional angiography dataset of a blood vessel tree of a patient, the system comprising:
a first interface configured to receive the angiography dataset;
a determination unit configured to determine a variant information describing a belonging to at least one anatomical variant class of a plurality of anatomical variant classes relating to anatomical variants of the blood vessel tree based on a comparison of angiography information of the angiography dataset to reference information describing at least one of the anatomical variant classes; and
a second interface configured to provide the variant information.

* * * * *